United States Patent [19]

Lott

[11] Patent Number: 4,718,689

[45] Date of Patent: Jan. 12, 1988

[54] URINARY COLLECTION BAG AND TUBING SUPPORT SYSTEM

[76] Inventor: Jacqulyn B. Lott, 4515 English Ct., R.R. 3, Bartow, Fla. 33830

[21] Appl. No.: 882,707

[22] Filed: Jul. 7, 1986

[51] Int. Cl.[4] .......................... A47C 7/62; A61F 5/44

[52] U.S. Cl. .................... 280/289 WC; 128/DIG. 24; 297/189; 297/DIG. 4; 604/326

[58] Field of Search ............... 280/289 WC, 242 WC; 297/DIG. 4, 188, 189, 192; 604/322, 326; 16/355; 248/95, 98, 100; 128/DIG. 24

[56] References Cited

U.S. PATENT DOCUMENTS

| | | | |
|---|---|---|---|
| 3,054,638 | 9/1962 | Johnson et al. | 297/188 X |
| 3,896,809 | 7/1975 | Samuel et al. | 297/DIG. 4 X |
| 3,931,650 | 1/1976 | Miller | 297/192 X |
| 4,050,117 | 9/1977 | Roy | 16/355 |
| 4,126,135 | 11/1978 | Hinman, Jr. | 604/326 |
| 4,146,265 | 3/1979 | Ocel et al. | 297/DIG. 4 X |
| 4,179,159 | 12/1979 | Sieklucki et al. | 604/322 X |

*Primary Examiner*—John J. Love
*Assistant Examiner*—Charles R. Watts
*Attorney, Agent, or Firm*—Pettis & McDonald

[57] ABSTRACT

A urinary collection bag and tubing support system intended for use in combination with a folding wheelchair. The system includes a tubing support mounted immediately below the wheelchair seat and a folding collection bag support removably attached to the wheelchair frame below the tubing support. The support system does not interfere with nor hinder the normal folding of the wheelchair, and need not be removed prior to folding the chair.

11 Claims, 4 Drawing Figures

URINARY COLLECTION BAG AND TUBING SUPPORT SYSTEM

BACKGROUND OF THE INVENTION.

1. Field of the Invention

The present invention relates to a urinary collection bag and tubing support system used in combination with a standard, folding wheelchair. The invention is particularly characterized by the construction and attachment of the system's tubing support and collection bag support to the wheelchair so that it can be left in place even when the chair is folded.

2. Description of the Prior Art.

Persons who are unable to control normal bladder functions are typically provided with a urinary catheter which is connected by tubing to a urinary collection bag. In hospital situations, the bag is normally hung from the foot of the patient's bed. However, in many instances, the patient is not entirely bedridden, but may require the assistance of a wheelchair for moving about. Thus, for patients fitted with a urinary catheter, some means must be provided in combination with the wheelchair for retaining the tubing and collection bag in a safe, sanitary and efficient manner.

Consideration of prior art patents reveals that devices for supporting urine collection bags are known. For example, U.S. Pat. No. 2,959,386 to Garth discloses a support for suspending bags and drain tubes at the side of a hospital bed. A functionally similar device is disclosed in U.S. Pat. No. 3,090,968 to Buono. Yet another bedside hanger construction is taught in U.S. Pat. No. 3,220,434 to Garth. Not only do each of these three patents specifically relate to means for hanging a collection bag from a bed, but also a study of the devices as disclosed in the patents confirms that none is particularly suited or intended for use in combination with a wheelchair. For example, none of these three patents disclose any means for retaining the relatively lengthy (usually about four feet) tubing interconnected between the catheter and the collection bag. Obviously, then, if any of these three devices were used in combination with a wheelchair, it probably would be necessary simply to place the tubing in the seat next to the patient. This could easily result in the formation of a kink or tight bend in the tubing, thereby restricting the flow of urine into the collection bag. Furthermore, it apparently would be necessary to suspend the devices taught in these three patents as from the side or arm of the wheelchair. Frankly, such would be relatively dangerous and certainly inconvenient, for the bag could restrict the patient's ability to propel the chair and, in any event, the bag could easily become entangled in the chair's wheel or spokes.

U.S. Pat. No. 4,179,159 to Sieklucki does describe and claim a urinary bag support specifically intended for use in combination with a conventional, foldable wheelchair. According to the disclosure of that patent, a pivoted arm is attached to the wheelchair below its seat. By pivoting the arm toward the rear of the chair, conventional folding of the chair may be accomplished. Without in any way questioning the utility of the device disclosed and claimed in this patent, it is nevertheless apparent that certain problems remain to be solved.

For example, the collection bag and tubing are placed in an envelope behind the patient's legs and under the wheel chair seat. Such placement is undesirable for the following reasons: (1) Obstructed visibility of the collection bag. Nursing personnel are responsible for continuous monitoring of not only the quantity of the catheterized patient's output, but also its quality. Constant visualization of the collection bag is necessary for the prompt detection of reportable abnormalities. It is impossible to monitor either the quantity or quality of the patient's urine when the collection bag is hidden from view within an enclosing envelope situated immediately behind a patient's legs, clothing and lap robe. (2) Inaccessibility. In order to empty the collection bag (done each shift in hospitals to obtain output records), one must first remove the tubing and collection bag from the supporting envelope. One must hold the collection bag and tubing with one hand while manipulating the drain valve with the other. This must be done while working through or around the patient's legs, clothing and lap robe. (3) It is unsafe, in many instances, for hospital personnel. Many catheterized patients are also confused and/or combative. While they would normally be restrained to the wheelchair, their hands and feet would not normally be restrained. Emptying of the collection bag cannot be accomplished with safety when it must be done within easy reach of the unrestrained hands and feet of confused and/or combative patients. Further problems are apparent in that placement of the tubing within the supporting envelope on top of the collection bag and under the securing top strap of the supporting envelope would require sharp bending of the tubing. Sharp bending of the tubing would restrict or stop the flow of urine to the collection bag and could result in patient discomfort or injury. Another problem is that the pivoting arm used to suspend the support envelope must be manually engaged with a receiving support bracket with each unfolding of the wheelchair and must be manually disengaged and pivoted rearward to accomplish refolding of the wheelchair. In hospitals, wheelchairs are routinely folded when not in use to comply with fire regulations that require unobstructed entry and exit ways. Manual manipulation of the pivoting arm with each folding and unfolding of the wheelchair is undesirable in that it increases the work load of hospital personnel.

It is therefore clear that there is a great need in the art for simple yet reliable means of supporting not only a urinary collection bag but also the associated tubing on a folding wheelchair in a manner that will not obstruct fluid flow through the tubing and into the bag, in a manner that will permit ready access to the bag, in a manner that will permit visibility of the collection bag's contents by nursing personnel, and in a manner that would permit the chair to be folded without necessarily having to remove the collection bag support system therefrom.

SUMMARY OF THE INVENTION

The present invention relates to a urinary collection bag and tubing support system for use in combination with a standard folding wheelchair. It is to be understood that while the wheelchair forms no part of the invention, the primary utility of this invention resides in its use in combination with a folding wheelchair.

The support system comprises a tubing support formed from a flexible material and attached to the wheelchair immediately below its seat. Attachment may be accomplished, for example, by the use of a plurality of fastener apertures formed along each outboard edge of the tubing support. A central segment of the tubing support is preferrably formed from an elastic material and has a pull tab attached to the front edge thereof. Accordingly, by pulling the tab, the tubing support will stretch to permit placement of drainage tubing on the support, below the seat. Because the size of the tubing support is substantially the same as that of the wheelchair seat, the drainage tubing may be placed therein without requiring severe bends in the tube. Furthermore, because the tube is stored beneath the seat, proper urinary drainage will be maintained.

The support system further includes a folding collection bag support attached to the frame of the wheelchair below the tubing support. Though described in greater detail hereinafter, the folding collection bag support is preferably formed from a relatively rigid material and, when open, or unfolded, defines a substantially V-shaped configuration. The junctions of the two sides defining the V-shaped configuration define a hinged attachement between the first support member and the second support member of the bag support so that the support may fold when the wheelchair is folded. The bag support is attached to the wheelchair frame by hooking the curved top edge of the first support member over a wheelchair frame element.

Inasmuch as standard folding wheelchairs are constructed to define a cross support system, the collection bag support is constructed so that it may be partially received by a cross support of the wheelchair. This construction is accomplished by providing first and second slots in the first and second support members, respectively. Each of the slots intersects, and substantially bisects, the hinged connection between the first and second support members, and each slot extends transversely from the bottom of the V toward the top. Thus, when operatively disposed onto the open wheelchair, a segment of the chair's cross support will extend through the open slot. The urinary collection bag, which is attached to the drainage tubing, is simply placed within the open collection bag support. Because the collection bag is disposed beneath the tubing, proper drainage is insured. Furthermore, because the collection bag is placed within the open V-shaped collection bag support, it is readily accessible for observation and maintenance from the rear of the wheelchair, well out of reach of confused or combative patients.

It should also be noted that it is not necessary to remove the support system of this invention from the wheelchair when it is desired to fold the wheelchair.

The invention accordingly comprises an article of manufacture possessing the features, properties and relation of elements which will be exemplified in the article hereinafter described, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION

Figure 1:
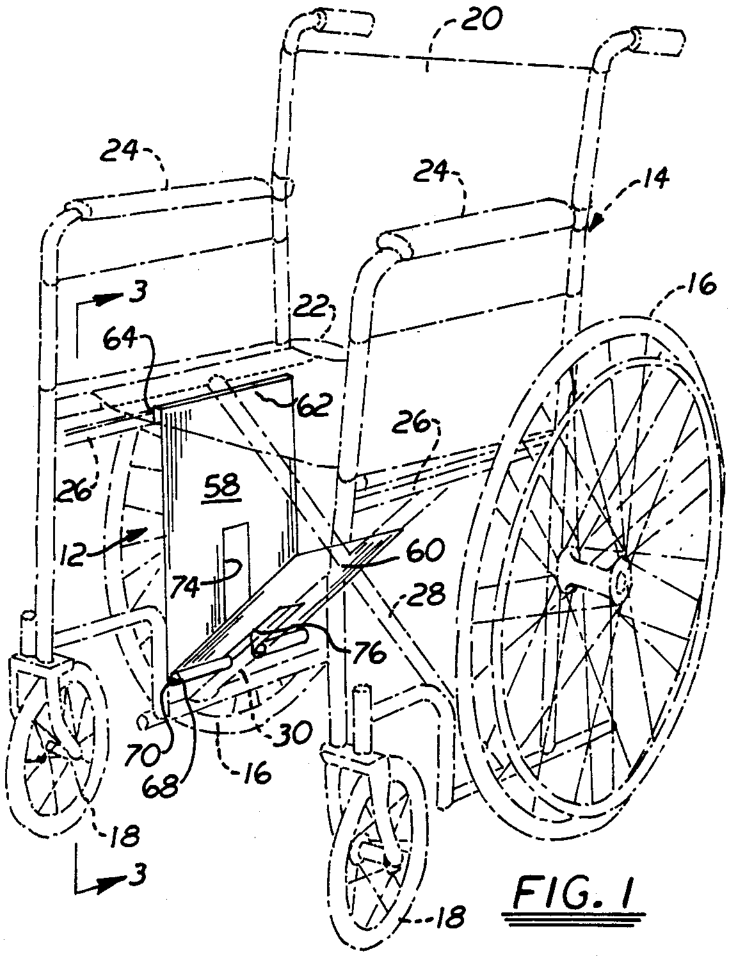
FIG. 1 is a perspective view showing attachment of the collection bag support to a standard folding wheelchair, with the chair shown in phantom.
Figure 2:
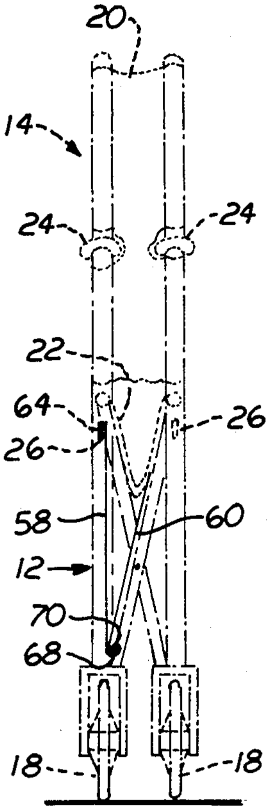
FIG. 2 is a front elevation of the chair shown in FIG. 1 folded.
Figure 3:
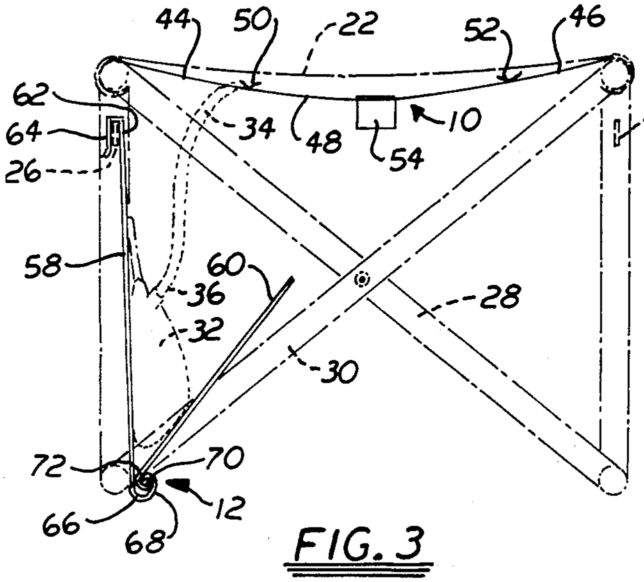
FIG. 3 is a fragmentary sectional view taken along line 3—3 of FIG. 1 showing the collection bag and tubing support system in greater detail.

As perhaps best seen in the more detailed view of FIG. 3, the urinary collection bag and tubing support system of this invention comprises a tubing support generally indicated as 10 and a folding collection bag support generally indicated as 12, both attached to and used in combination with a standard cross-supported folding wheelchair generally indicated as 14 in the views of FIGS. 1 and 2. Inasmuch as wheelchair 14 is not claimed as part of the invention, per se, it and its elements are shown in phantom throughout the several views of the drawings. As can be seen, however, chair 14 is of standard construction including rear wheels 16, front wheels 18, a back 20, a seat 22, arm rests 24, side frames 26, and cross supports 28 and 30. Attention is also invited to the fact that in the view of FIG. 3, urinary collection bag 32 is shown in phantom as well as a segment of drainage tubing 34 one end 36 of which is operatively connected to bag 32.

Figure 4:
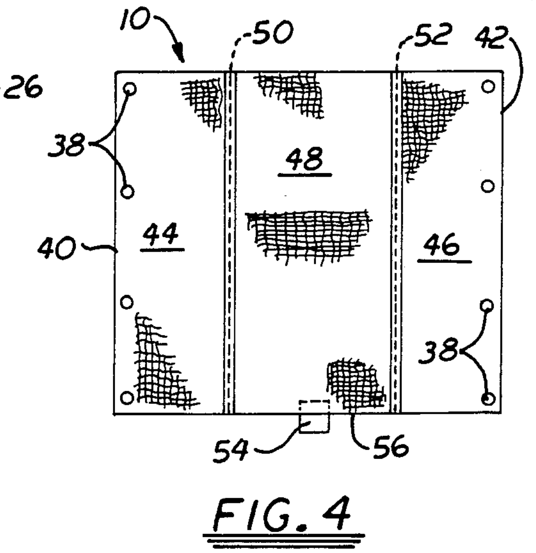
FIG. 4 is a top plan view of the tubing support of this invention.

Considering first the view of FIG. 4, it can be seen that tubing support 10 comprises a plurality of attachment means 38 formed along opposite, substantially parallel edges 40 and 42 of tubing support 10. Each of the attachment means 38 may comprise, for example, snaps, buttons, hooks, or button holes. Regardless of the specific construction of attachment means 38, they are used to mount tubing support 10 immediately below seat 22 as best seen in the view of FIG. 3.

Outboard segments 44 and 46 of tubing support 10 may be formed from virtually any flexible material; however, central segment 48 is preferably formed from an elastic material. As shown at lines 50 and 52, central segment 48 preferably interconnects outboard segments 44 and 46 by a sewn seam. For convenience in providing access to the receptacle defined between tubing support 10 and seat 22, a pull tab 54 is attached to front edge 56 of elastic central segment 48.

As best seen in the view of FIGS. 1 and 3, the folding collection bag support 12 comprises a first support member 58 and a second support member 60, both of which are formed from a relatively rigid material, preferrably metal for ease of cleaning. Also as clearly shown in the view of FIG. 3, and as described in greater detail below, first support member 58 and second support member 60 are hingedly attached to each other. The width of each of the support members 58 and 60 are substantially equal, and each width is less than the length of its corresponding member.

As most clearly seen in the view of FIG. 3, the top edge of first member 58 is curved away from second member 60 to define a first support member hook 64. As shown in FIG. 3, hook 64 may be placed in partially surrounding relation to a segment of side frame 26 for the purpose of removably attaching folding collection bag support 12 to wheelchair 14.

Bottom edge 66 of first support member 58 is curved toward second support member 60 to define a first hinge curl 68. A corresponding second hinge curl 70 is formed on second support member 60 by curving its bottom edge 72 away from first support member 58. Thus, by sliding first hinge curl 68 along the width of second hinge curl 70, a hinged, pivoting connection between first support member 58 and second support member 60 is provided.

Referring to the view of FIG. 1, it can be seen that first support member 58 further comprises a first slot 74 formed therein. First slot 74 intersects first hinge curl 68 and extends transversely therefrom toward first support member hook 64. A corresponding second slot 76 is formed in second support member 60. Second slot 76 intersects second hinge curl 70 and extends transversely therefrom in corresponding relation to first slot 74. As may be seen in the views of both FIGS. 1 and 3, first slot 74 and second slot 76 permit segments of cross support 30 to pass therethrough, providing further support and stabilization for folding collection bag support 12.

Having thus set forth a preferred construction for the urinary collection bag and tubing support system of this invention, its utility, efficiency and safety may be easily appreciated. Once tubing support 10 and folding collection bag support 12 have been attached to the wheelchair 14, it is not necessary that they be removed, for they do not inhibit at all any normal use of the wheelchair 14. Any excess drainage tubing 34 is conveniently and safely stored on tubing support 10 below the patient's bladder, and urinary collection bag 32 is conveniently stored therebelow on folding collection bag support 12. Both bag 32 and tubing 34 are maintained for proper drainage while at the same time being entirely removed and protected from becoming entangled with elements of chair 14, the patient, or any other structure present in the environment wherein chair 14 is being used.

It will thus be seen that the objects set forth above, among those made apparent from the preceding description, are efficiently attained and, since certain changes may be made in the above article without departing from the scope of the invention it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of lanquage, might be said to fall therebetween.

Now that the invention has been described,

What is claimed is:

1. A urinary collection bag and tubing support system for use in combination with a folding wheelchair having a seat, a frame and cross supports, said support system comprising: a tubing support formed from a flexible material and attached to the frame of the folding wheelchair underneath the seat thereof such that said tubing support is folded in response to folding of the wheelchair; and a folding collection bag cradling support including a first substantially rigid support member removably attached to the wheelchair frame below said tubing support and a second substantially rigid support member hingedly attached to said first support member and being engagable by a cross support such that said second support member is folded relative to said first support member in response to folding of the wheelchair, whereby a urinary collection bag may be cradled by said collection bag cradling support in operative, fluid receiving relation to one end of a length of urinary tubing, at least a portion of the length of the tubing being placed on said tubing support and the other end of the tubing being attachable in fluid communicating relation to a catheter.

2. A urinary collection bag and tubing support system as in claim 1 wherein said tubing support comprises attachment means formed along opposite, substantially parallel edges of said flexible material, whereby said tubing support may be attached to the folding wheelchair.

3. A urinary collection bag and tubing support system as in claim 2 wherein said tubing support further comprises an elastic panel interconnecting said opposite, substantially parallel edges.

4. A urinary collection bag and tubing support system as in claim 3 wherein said tubing support further comprises a pull tab attached to said elastic panel intermediate said opposite edges and extending outwardly from said elastic panel toward the front of the wheelchair, whereby said tubing support may be pulled away from the wheelchair seat.

5. A urinary collection bag and tubing support system as in claim 1 wherein said first and second support members each define substantially rectangular perimeters wherein the width of each of said members is substantially equal one to the other, and wherein said width is less than the length of each of said members.

6. A urinary collection bag and tubing support system as in claim 5 wherein the top edge of said first support member defines said first support member width and is curved away from said second support member to define a first support member hook, whereby said collection bag support may be removably attached to the wheelchair frame.

7. A urinary collection bag and tubing support system as in claim 6 wherein the bottom edge of said first support member is curved toward said second support member to define a first hinge curl.

8. A urinary collection bag and tubing support system as in claim 7 wherein the bottom edge of said second support member defines said second support member width and is curved away from said first support member to define a second hinge curl, said first and second hinge curls being engageable one with the other whereby said collection bag support may fold.

9. A urinary collection bag and tubing support system as in claim 8 wherein said first and second support members further comprise corresponding first and second slots formed therein, said first slot intersecting said first hinge curl and extending transversely therefrom toward said first support member hook and said second slot intersecting said second hinge curl and extending transversely therefrom in corresponding relation to said first slot, whereby said collection bag support may be partially received by a cross support of the wheelchair.

10. A urinary collection bag and tubing support system for use in combination with a folding wheelchair having a seat, a frame and cross supports, said support system comprising:

a tubing support formed from a flexible material and including means formed along opposite, substantial parallel edges of said flexible material for attaching said tubing support to the frame of the folding wheelchair underneath the seat thereof such that said tubing support is folded in response to folding of the wheelchair, said tubing support further comprising an elastic panel interconnecting said opposite substantially parallel edges, and a pull tab attached to said elastic panel intermediate said opposite edges and extending outwardly from said elastic panel toward the front of the wheelchair, whereby said tubing support may be pulled away from the wheelchair seat;

a folding collection bag support including a first substantially rigid support member removably attached to the wheelchair frame below said tubing support and a second substantially rigid member hingedly attached to said first support member and being engagable by a cross support such that said second support member is folded relative to said first support member in response to folding of the wheelchair, whereby a urinary collection bag may be placed within said collection bag support in operative, fluid receiving relation to one end of the length of urinary tubing, at least a portion of the length of the tubing being placed on said tubing support and the other end of the tubing being attachable in fluid communicating relation to a catheter.

11. A urinary collection bag and tubing support system for use in combination with a folding wheelchair having a seat, a frame and cross suppports, said support system comprising a tubing support formed from a flexible material and attached to the frame of the folding wheelchair below the seat thereof such that said tubing support is folded in response to folding of the wheelchair; and a folding collection bag support including a first substantially rigid support member removably attached to the wheelchair frame below said tubing support and a second substantially rigid support member hingedly attached to said first support member and being engagable by a cross support such that said second support member is folded relative to said first support member in response to folding of the wheelchair, said first and second support members each defining substantially rectangular perimeters wherein the width of each of said members is substantially equal one to the other, and wherein said width is less than the length of each said members, the top edge of said first support member defining said first support member width and being curved away from said second support member to define a first support member hook whereby said collection bag support may be removably attached to the wheelchair frame, the bottom edge of said first support member being curved toward said second support member to define a first hinge curl, the bottom edge of said second support member defining said second support member width and being curved away from said first support member to define a second hinged curl, said first and second hinged curls being engagable one with the other whereby the collection bag support may fold, said first and second support members further comprising corresponding first and second slots formed therein, said first slot intersecting said first hinge curl and extending transversely therefrom toward said first support member hook and said second slot intersecting said second hinge curl and extending transversely therefrom in corresponding relation to said first slot, whereby said collection bag support may be partially received by a cross support of the wheelchair, and a urinary collection bag may be placed within said collection bag support in operative, fluid receiving relation to one end of a length of urinary tubing, at least a portion of the length of the tubing being placed on said tubing support and the other end of the tubing being attachable in fluid communication relation to a catheter.

* * * * *